US00PP17085P3

(12) United States Plant Patent
Nyström

(10) Patent No.: US PP17,085 P3
(45) Date of Patent: Sep. 5, 2006

(54) BOXWOOD PLANT NAMED 'POLAR'

(50) Latin Name: *Buxus sempervirens*
Varietal Denomination: Polar

(75) Inventor: Per Nyström, Vislanda (SE)

(73) Assignee: Sveplants E-grupp ekonomisk förening, Helsingborg (SE)

( * ) Notice: Subject to any disclaimer, the term of this patent is extended or adjusted under 35 U.S.C. 154(b) by 0 days.

(21) Appl. No.: 11/114,603

(22) Filed: Apr. 25, 2005

(65) Prior Publication Data

US 2005/0198718 P1 Sep. 8, 2005

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

UPOV–ROM GTITM, Plant Variety Database, 2005/04, GTI Jouve Retrieval Software, Citation for *Buxus 'Polar'*.* Vegetation and Technology in Partnership [online], [retrieved on Jan. 4, 2006]. Retrieved from the Internet <http://www.vegtech.se/english.htm> one page only.*

* cited by examiner

*Primary Examiner*—Kent Bell
*Assistant Examiner*—June Hwu
(74) *Attorney, Agent, or Firm*—Penny J. Aguirre

(57) ABSTRACT

A new and distinct cultivar of *Buxus sempervirensn*, 'Polar', found in a province of Sweden where the climate is cold (representing zone 4 of the Swedish Hardiness Map) that exhibits exceptional winter hardiness. 'Polar' is further characterized by a dense, compact, and medium to broad growth habit and evergreen foliage with leaves that are broadly elliptic in shape, shiny in appearance, and dark green in color that exhibits no substantial change in coloration during the winter. 'Polar' is well suited for topiary and for use in parks and gardens in cold climates, where other Boxwood cultivars are inappropriate.

3 Drawing Sheets

Genus/species: *Buxus sempervirens.*
Varietal denomination: 'Polar'.

BACKGROUND OF THE INVENTION

The present invention relates to a new and distinct cultivar of *Buxus sempervirens* and will be referred to hereafter by its cultivar name 'Polar'. 'Polar' was discovered as a naturally-occurring whole plant variant in a cultivated area in the province of Småland in southern Sweden in 1995 by the inventor. The parentage is unknown, but is presumed to have been derived originally from a cutting of an unnamed plant of *Buxus sempervirens*. The climate in the province is very cold, representing zone 4 of the Swedish Hardiness Map. The age of the plant is unknown, however is thought to have existed and survived through the cold winters of the 1940s, when temperatures went below minus 40° Celsius.

'Polar' is a dense, medium to broad, compact woody broad-leaf evergreen that produces in an attractive ornamental plant even in colder climates, where other Boxwood cultivars produce unsatisfactory plants. The use of Boxwood in Swedish parks and gardens and other cold climates has to date been limited due to lack of hardy cultivars available on the market. The compact habit of 'Polar' makes it well suited for topiary as well.

The new cultivar can also be characterized by its shiny, dark green, foliage comprised of broadly elliptic leaves, with good winter color retention and resistance to winter burn.

Winter compared to the species *Buxus sempervirens* and the cultivars normally used in Sweden, ('Rotundifolia' (not patented), 'Vrams Gunnarstorp' (not patented), 'Faulkner' (not patented), 'Arborescens' (not patented) and 'Blauer Heinz' (not patented), 'Polar' is more dense, compact and sturdy and exhibits superior cold hardiness. 'Polar' can at least be grown up to zone 4 (according to the Swedish Hardiness Map), while the others can be grown only to zone 2 or zone 3. 'Polar' differs in plant habit in comparison to the cultivar, 'Green Ice'. (U.S. Plant Pat. No. 10,773), in that 'Green Ice' is more upright in habit while 'Polar' develops into a plant habit where its width exceeds its height.

The leaves of 'Polar' are wider compared to the species *Buxus sempervirens* and the cultivars 'Vrama Gunnarstorp', 'Faulkner', 'Handsworthiensis' (not patented), and 'Blauer Heinz'. The leaves of the cultivar 'Rotundifolia' are broad, but they are rounder and larger than the leaves of 'Polar'.

Asexual reproduction of 'Polar' by stem cuttings was first conducted in 1995 by the inventor in Jonstorp, Sweden and propagation continued for a period of 8 years. This propagation has confirmed that the unique characteristics of 'Polar' are stable and are reproduced true to type in successive generations.

SUMMARY OF THE INVENTION

The following traits have been repeatedly observed and represent the characteristics of the new cultivar, with observations made both on the original discovered plant and three year-old plants grown in a nursery in southern Sweden. These attributes in combination distinguish 'Polar' from other varieties of *Buxus sempervirens* known to the inventor.

1. Exhibits excellent winter hardiness to at least zone 4 (according to the Swedish Hardiness Map).
2. Dense, compact, medium to broad growth habit suitable as an ornamental specimen or for use in topiary. When not used for topiary its width commonly exceeds its height.

3. Has foliage that is shiny and very dark green above and brown green below. The shiny dark green coloration of the foliage is well maintained even during winter, the foliage resists the tendency to assume brown-green foliage coloration during the winter as is typical of other cultivars. Good resistance to winter burn is also exhibited.
4. Broad elliptic leaves.
5. Very vital with a vigorous growth rate, resistant to diseases, and tested negative for the presence of viruses known to affect Boxwood.
6. Readily propagated asexually by stem cuttings.

BRIEF DESCRIPTION OF THE DRAWING

The accompanying photographs show typical characteristics of the cultivar 'Polar'. The photographs in FIG. 1 and FIG. 2 were taken in May 2004 and the photographs in FIG. 3 and FIG. 4 were taken in November 2003.

FIG. 3 illustrates the growth and development in the nursey, while FIG. 4 illustrates the shoots and leaves of 'Polar' and shows the broad elliptic shape of the leaves and the rounded, or slightly notched, apex.

Figure 1:
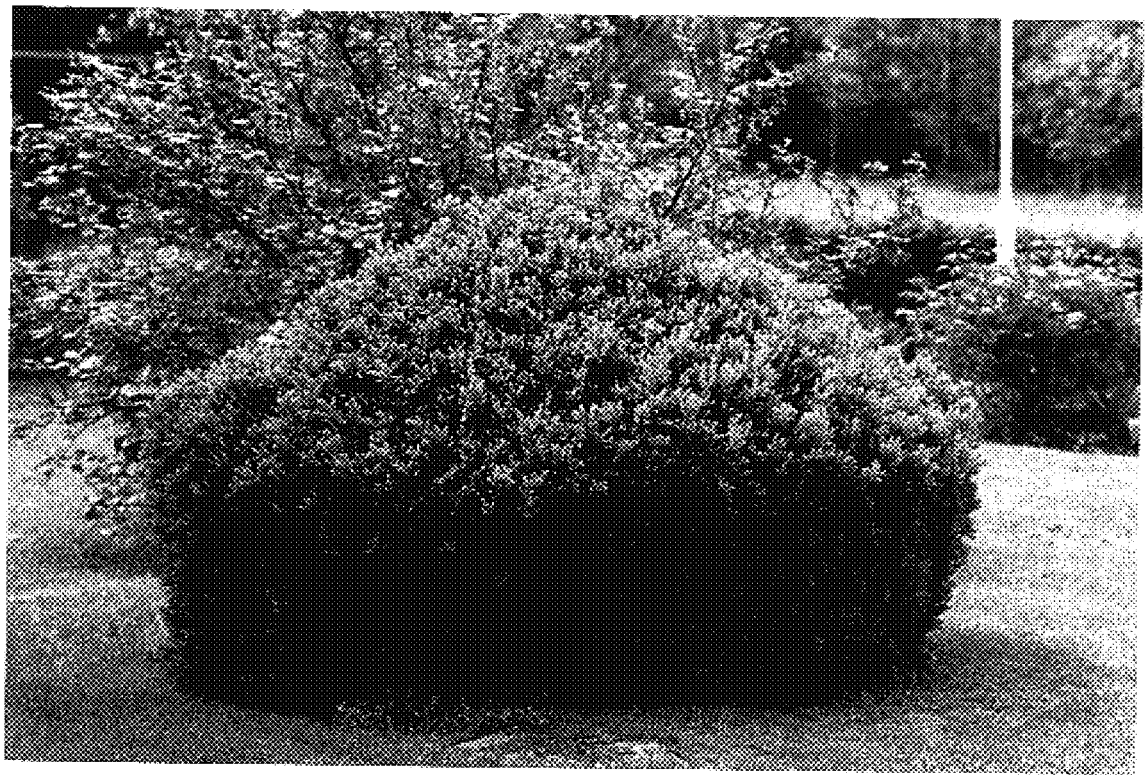
FIG. 1 and FIG. 2 illustrate the original plant of the new cultivar and shows its suitability for topiary. The exact age of the plant is unknown. The photographs show the dense, compact and sturdy growth habit. It also shows how well 'Polar' develops in the harsh climate in zone 4 (according to the Swedish Hardiness Map).
Figure 2:
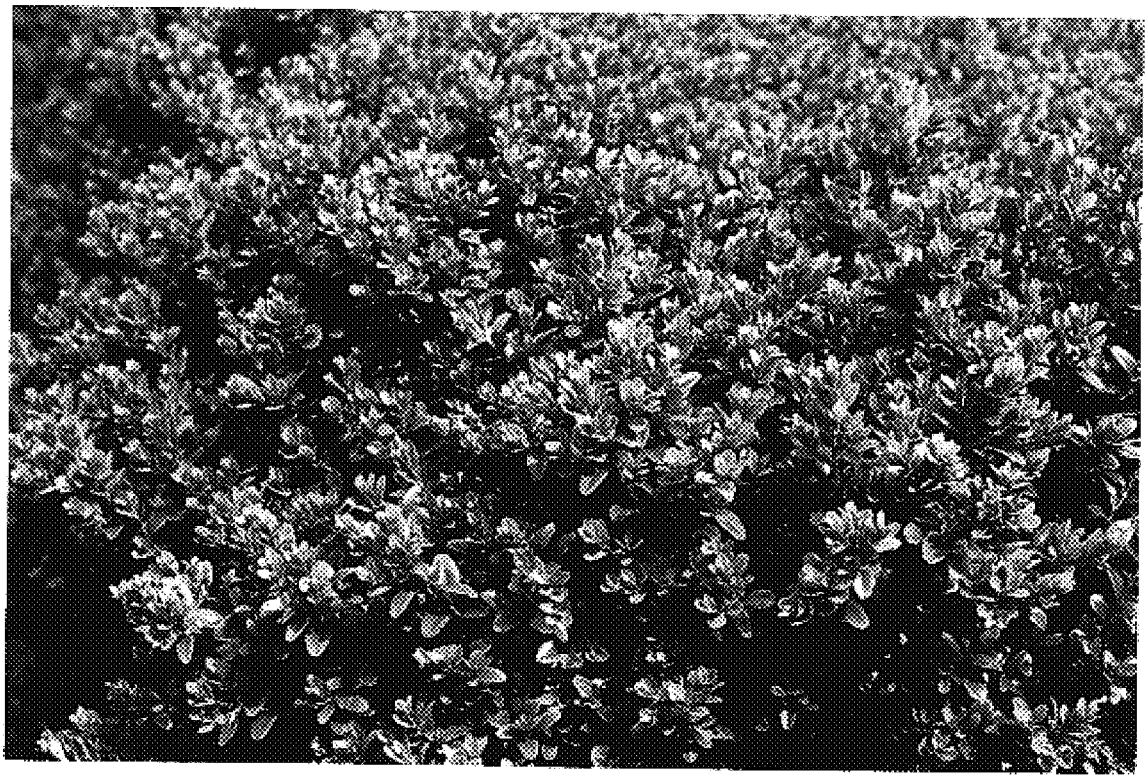
Figure 3:
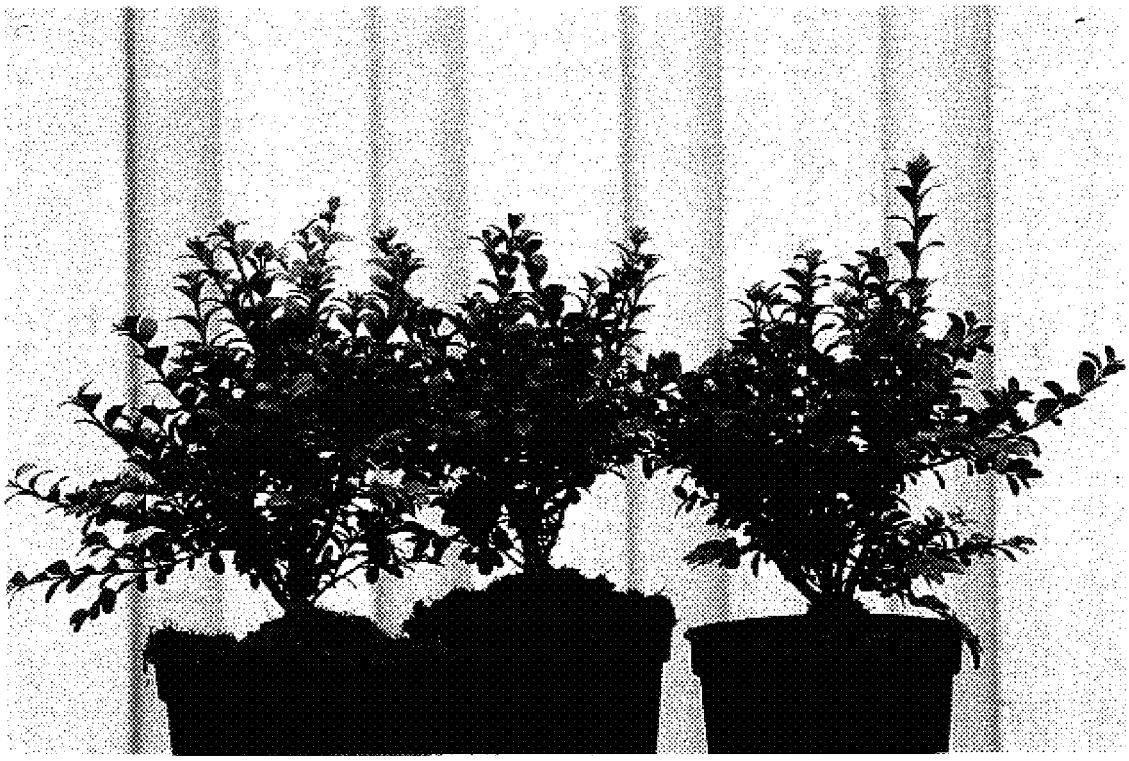
FIG. 3 and FIG. 4 illustrate three-year-old plants in a nursery in southern Sweden.
Figure 4:
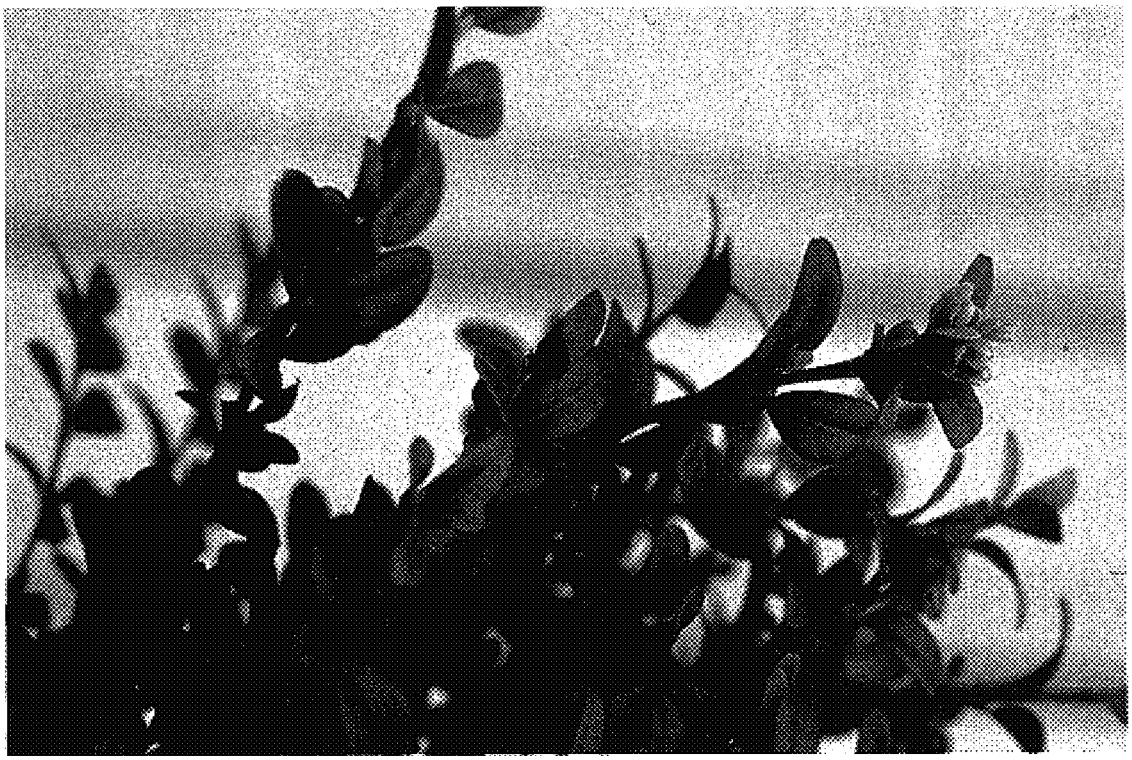
Figure 5:
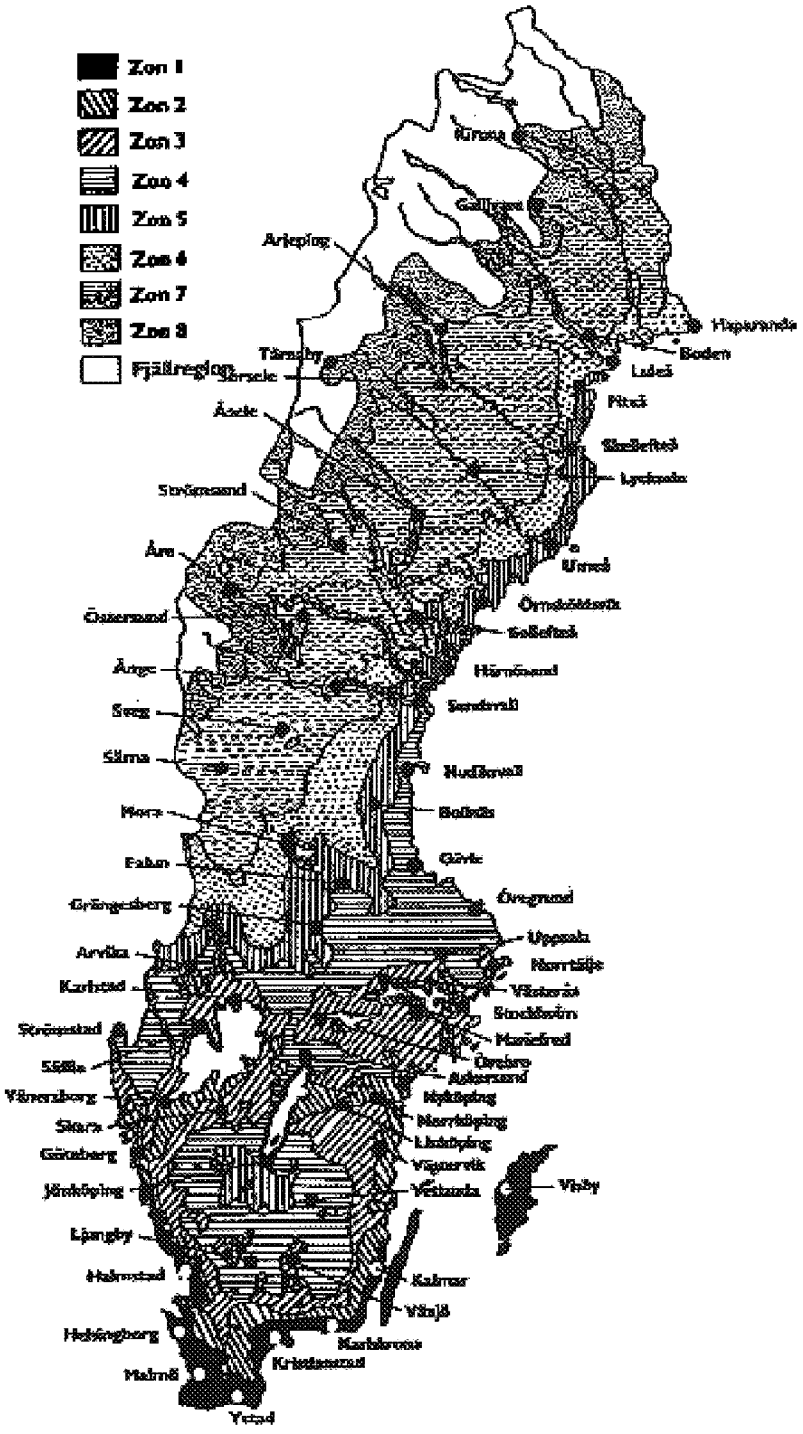
FIG. 5 is a Swedish Hardiness Map, the Zones are depicted in variable shading patterns and correspond to the legend, with zones depicted as Zon 1 through Zon 8 (correspond to zones 1 through 8 in the description) plus a fjällregion zone. The labels correspond to cities in Sweden. The hardiness map is based on a combination of environmental conditions with the larger numbers depicting harsher conditions.

The colors in the photographs are as close as possible with conventional photography and the color readings in the detailed botanical description accurately describe the new cultivar.

BOTANICAL DESCRIPTION OF THE PLANT

The following is a detailed description of the cultivar 'Polar', which was prepared while observing the original plant and several three year-old plants grown outdoors in containers in a nursery in southern Sweden. Testing was also conducted on plants grown in several nurseries and other testing sites throughout Sweden. The new cultivar has not been tested under all possible sets of conditions and phenotypic differences may be observed with variations in environmental, climatic, and cultural conditions. Color terminology is in accordance with The R.H.S. Colour Chart of The Royal Horticultural Society, London, England, except where terms of ordinary significance are used.

Botanical classification: A cultivar of *Buxus sempervirens*, named 'Polar'.

Type: Hardy broad-leafed evergreen shrub for garden decoration and general landscape use.

Parentage: 'Polar' was discovered as a whole plant mutation and is presumed to have been derived originally from a cutting of an unnamed plant of *Buxus sempervirens*.

Growth habit: The growth habit is dense, medium to broad, compact and very sturdy.

Growth rate: Grows slowly, about 50 mm per year. A three year-old plant from a rooted cutting reaches up to about 25 cm in height and about 25 cm in width. After additional years, the width exceeds its height.

Mature plant dimensions: The ultimate size and crown shape is not yet known since the mother plant was found in a clipped hedge.

Hardiness: The original plant was found in a province of Sweden where the climate is cold, representing zone 4 of the Swedish Hardiness Map (©Riksförbundet Svensk Trädgårds (RST) Växtatlas 1993). 'Polar' has been situated at the original place since at least the 1940's. During the winters of the 1940's, the temperatures were extremely low (below minus 40° Celsius), but this plant has survived and developed without any damage. The cultivar also surived the winter 2003/2004 without any winter damages in the village 'Burträsk', situated in northern Sweden, zone 6. 'Polar' has also been tested in different nurseries in Sweden since 1996 located in Vislanda (zone 3), Nossebro (zone 2) and Jonstorp (zone 1) and in testing sites at different places in Sweden, particularly to evaluate the limit of hardiness located in Uppsala (zone 3), Skellefteå (zone 5), and Piteå (zone 5).

Diseases resistance: The cultivar 'Polar' seems to be very healthy, and no disease problems have been observed to date. The cultivar has been tested for viruses with negative result.

Insect resistance: No insect damage has been observed to date.

Root description: Fibrous.

Growth and propagation:

*Propagation.*—Stem cuttings, semi hardwood.

*Root initiation.*—Time required for root development depends on time for propagation. The fastest rooting initiating is received when cuttings are taken in early autumn. Then it takes 4 to 6 weeks grown at 20° Celsius in a greenhouse without supplemental lighting.

*Time required for root development.*—Depends on growing conditions. A 0,8 liter container potted with a 93 milliliter plug is well rooted and saleable in 3 to 4 months when grown in a poly tent. The rooting and growing substrate should be well drained.

Branch description:

*Branch shape.*—Quadrangular, young branches slightly winged, mature branches lack wings.

*Branch color.*—Young shoots; yellow-green 145A, wings darker yellow-green 144A.

*Mature shoots.*—Yellow-green 152B.

*Branch diameter.*—Variable, depending on the age of the plants. Generally the branch diameter is greater in comparison to other cultivars of *Buxus sempervirens*.

*Branch surface.*—Glabrous.

Foliage description:

*Fragrance.*—The foliage has a less strong scent than is typical of other cultivars of *Buxus sempervirens*.

*Lamina shape.*—Broadly elliptic.

*Lamina division.*—Simple.

*Lamina base.*—Base cuneate.

*Lamina apex.*—Rounded or slightly notched.

*Lamina margins.*—Entire.

*Lamina size.*—2.2 to 2.5 cm in length and 1.3 to 1.5 cm in width.

*Lamina surface.*—Upper surface is shiny, lower surface is glabrous. Minute hairs are present at the base.

*Lamina color.*—New growth; upper and lower surface 144A in color. Mature; upper surface is very dark green 139A and lower surface is brown-green 146D, color is retained in winter months and the foliage is resistant to winter burn.

*Lamina venation.*—Midrib is conspicuous and 138B in color.

*Petiole description.*—2 mm in length, 138B in color, minute hairs.

Flower description: No flower or fruit production has been observed on the original plant or on any propagated plants of 'Polar' with the exception of one three year-old plant exposed to the stresses of drought and lack of fertilizer. The small petal-less flowers appeared in clusters in the leaf axils with each cluster containing numerous (about 25) male flowers (color 154C) surrounding a single female flower (color (143C). Due to the rare occurrence of flowering, more flower data in more detail is unavailable.

It is claimed:

1. A new and distinct cultivar of Boxwood plant named 'Polar' substantially as herein illustrated and described.

* * * * *

RST:s Zonkarta
över Sverige